US00PP16400P2

(12) United States Plant Patent
Verheijen

(10) Patent No.: US PP16,400 P2
(45) Date of Patent: Apr. 4, 2006

(54) ***HYPERICUM* PLANT NAMED 'VERPUTA'**

(50) Latin Name: *Hypericum androsaemum*
Varietal Denomination: Verputa

(75) Inventor: Edwin Martijn Verheijen, Wieringerwerf (NL)

(73) Assignee: Handelskwekerij Verheijpn Vof, Wieringerwerf (NL)

( * ) Notice: Subject to any disclaimer, the term of this patent is extended or adjusted under 35 U.S.C. 154(b) by 102 days.

(21) Appl. No.: 10/923,983

(22) Filed: Aug. 23, 2004

(51) Int. Cl.
*A01H 5/00* (2006.01)

(52) U.S. Cl. ..... Plt./263
(58) Field of Classification Search ..... Plt./263
See application file for complete search history.

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Hypericum* plant named 'Verputa', characterized by its upright and outwardly spreading plant habit; dark green leaves; yellow-colored fruits; good postproduction longevity; and resistance to Rust.

2 Drawing Sheets

Botanical classification/cultivar designation: *Hypericum androsaemum* cultivar Verputa.

BACKGROUND OF THE INVENTION

The present Invention relates to a new and distinct cultivar of *Hypericum* plant, botanically known as *Hypericum androsaemum*, commercially used as cut stems with fruits, and hereinafter referred to by the name 'Verputa'.

The new *Hypericum* is a product of a planned breeding program conducted by the Inventor in Wieringerwerf, The Netherlands. The objective of the breeding program was to develop cut *Hypericum* varieties with attractive fruit coloration.

The new cultivar originated from a cross-pollination made by the Inventor in 1998 of a proprietary seedling selection of *Hypericum* identified as code number 21047, not patented, as the female, or seed, parent with a proprietary seedling selection of *Hypericum* identified as code number MP1, not patented, as the male, or pollen, parent. The cultivar Verputa was discovered and selected by the Inventor in 2000 as a flowering plant within the progeny of the stated cross-pollination in a controlled environment in Wieringerwerf, The Netherlands.

Asexual reproduction of the new *Hypericum* by terminal cuttings at Wieringerwerf, The Netherlands, has shown that the unique features of this new *Hypericum* are stable and reproduced true to type in successive generations of asexual reproduction.

SUMMARY OF THE INVENTION

The following traits have been repeatedly observed and are determined to be the unique characteristics of 'Verputa'. These characteristics in combination distinguish 'Verputa' as a new and distinct cultivar:

1. Upright and outwardly spreading plant habit.
2. Dark green-colored leaves.
3. Yellow-colored fruits.
4. Good postproduction longevity.
5. Resistant to Rust.

Plants of the new *Hypericum* differ from plants of the parent seedling selections primarily in fruit coloration.

Plants of the new *Hypericum* can be compared to plants of the *Hypericum* cultivar Excellent Flair, not patented. In side-by-side comparisons conducted in Wieringerwerf, The Netherlands, plants of the new *Hypericum* differed from plants of the cultivar Excellent Flair in the following characteristics:

1. Plants of the new *Hypericum* had darker green-colored leaves than plants of the cultivar Excellent Flair.
2. Leaves of plants of the new *Hypericum* did not sun scorch whereas leaves of plants of the cultivar Excellent Flair sun scorched.
3. Fruits of plants of the new *Hypericum* were yellow in color whereas fruits of plants of the cultivar Excellent Flair were brownish red in color.

BRIEF DESCRIPTION OF THE PHOTOGRAPHS

The accompanying colored photographs illustrate the overall appearance of the new *Hypericum*, showing the colors as true as it is reasonably possible to obtain in colored reproductions of this type. Colors in the photographs may differ slightly from the color values cited in the detailed botanical description which accurately describe the colors of the new *Hypericum*.

The photograph on the first comprises a side perspective view of a typical flowering stem of 'Verputa'.

The photograph at the top of the second sheet is a close-up view of typical fruits of 'Verputa'.

The photograph at the bottom of the second sheet is a close-up view of a typical flower with a developing fruit of 'Verputa'.

DETAILED BOTANICAL DESCRIPTION

The new *Hypericum* has not been observed under all possible environmental conditions. The phenotype may vary somewhat with variations in environment such as temperature, daylength and light intensity, without, however, any variance in genotype.

The aforementioned photographs, following observations and measurements describe plants grown in Quito, Ecuador, in an outdoor nursery and under commercial production practices. Plants were about two years old. The photographs and description were taken during the spring with average day temperatures of about 17° C. and average night temperatures of about 11° C. In the following description, color references are made to The Royal Horticultural Society Colour Chart, 2001 Edition, except where general terms of ordinary dictionary significance are used.

Botanical classification: *Hypericum androsaemum* cultivar Verputa.

Parentage:

*Female parent*.—Proprietary seedling selection of *Hypericum androsaemum* identified as code number 21047, not patented.

*Male parent*.—Proprietary seedling selection of *Hypericum androsaemum* identified as code number MP1, not patented.

Propagation:

*Type*.—Terminal cuttings.

*Time to produce a rooted cutting*.—About 30 days at 20° C.

*Root description*.—Freely branching; medium thickness; grayed orange in color.

Plant description:

*Plant form*.—Upright and outwardly spreading perennial woody shrub; globular.

*Growth habit*.—Moderately vigorous. Freely basal branching; dense and bushy growth habit.

*Plant height*.—About 90 cm.

*Plant width* (*spread*).—About 75 cm.

*Quantity of stems per year*.—About 15.

*Lateral branches*.—Length: About 11 cm. Diameter: About 2 mm. Internode length: About 2.7 cm. Strength: Moderate. Texture: Smooth; glabrous. Color, upper and lower surfaces: 144C.

*Foliage description*.—Leaves opposite; single; sessile and generally symmetrical. Length: About 5.5 cm. Width: About 2.6 cm. Shape: Ovate. Apex: Obtuse to acute. Base: Obtuse. Margin: Entire. Texture, upper and lower surfaces: Glabrous; slightly rugose. Venation pattern: Pinnate. Color: Developing leaves, upper surface: 141A. Developing leaves, lower surface: 141C. Fully expanded leaves, upper surface: 137A; venation, 145B to 145C. Fully expanded leaves, lower surface: 138B; venation, 139D.

Flower description:

*Flower type and habit*.—Bright yellow single flowers arranged in terminal compound umbels with about eleven flowers per umbel; about 24 flowers and flower buds per lateral branch. Flowers not fragrant. Flowers not persistent. Flowers face mostly upright.

*Natural flowering season*.—Summer, typically July in Wieringerwerf, The Netherlands; flowering period typically lasts about 35 days.

*Postproduction longevity*.—Cut flower are typically harvested when all flowers have developed fruits. Postproduction longevity of cut stems with fruits is about two weeks.

*Inflorescence height*.—About 6 cm.

*Inflorescence diameter*.—About 4.3 cm.

*Flower buds*.—Height: About 9 mm. Diameter: About 7 mm. Shape: Ovoid. Color: 13A; towards apex, N30C.

*Flowers*.—Diameter: About 2.4 cm. Depth: About 1.4 cm.

*Petals*.—Quantity per flower: Five. Length: About 1.2 cm. Width: About 1 cm. Shape: Broadly elliptic to broadly obovate. Aspect: Concave. Apex: Obtuse to acute. Base: Attenuate. Margin: Entire. Texture, upper and lower surfaces: Smooth; glabrous. Color: Developing and fully expanded petals, upper surface: 15B; color does not fade with subsequent development. Developing and fully expanded petals, lower surface: 16C.

*Sepals*.—Quantity per flower: Five. Length: About 1 cm. Width: About 8 mm. Shape: Ovate. Aspect: Convex. Apex: Obtuse to acute. Base: Broadly cuneate. Margin: Entire. Texture, upper and lower surfaces: Smooth; glabrous. Color: Developing and fully expanded sepals, upper surface: 144C. Developing and fully expanded sepals, lower surface: 145A.

*Peduncles*.—Length: About 1.1 cm. Diameter: About 1.1 mm. Orientation: Erect to about 10° from vertical. Strength: Moderately strong. Color: 138D.

*Pedicels*.—Length: About 1.2 cm. Diameter: About 1.1 mm. Orientation: Erect to about 60° from vertical. Strength: Moderately strong. Color: 138D.

*Reproductive organs*.—Stamens: Quantity per flower: About 70 to 80. Stamen length: About 1.1 cm. Filament color: 13A. Anther shape: Broadly ovate. Anther length: About 0.5 mm. Anther color: 23C. Pollen amount: Moderate. Pollen color: 23C. Pistils: Quantity per flower: Three. Pistil length: About 8 mm. Stigma shape: Globular. Stigma color: 63A. Style length: About 3 mm. Style color: 154C. Ovary color: 154C.

*Fruits*.—Quantity per flower: One. Days to ripening: About 25. Longevity on the plant: About 30 days. Type: Capsule. Shape: Ellipsoidal. Length: About 1.3 cm. Diameter: About 1.1 cm. Texture: Smooth; glabrous. Color: 2C; towards the apex, 167B.

*Seeds*.—Quantity per fruit: More than 100. Length: About 0.8 mm. Diameter: About 0.5 mm. Texture: Smooth; glabrous. Color: 199A to N199A.

Disease/pest resistance: Plants of the new *Hypericum* have been observed to be resistant to Rust. Plants of the new *Hypericum* have not been observed to be resistant to pests and other pathogens common to *Hypericum*.

Temperature tolerance: Plants of the new *Hypericum* have been observed to tolerate temperatures ranging from −15 to 35° C.

It is claimed:

1. A new and distinct cultivar of *Hypericum* plant named 'Verputa', as illustrated and described.

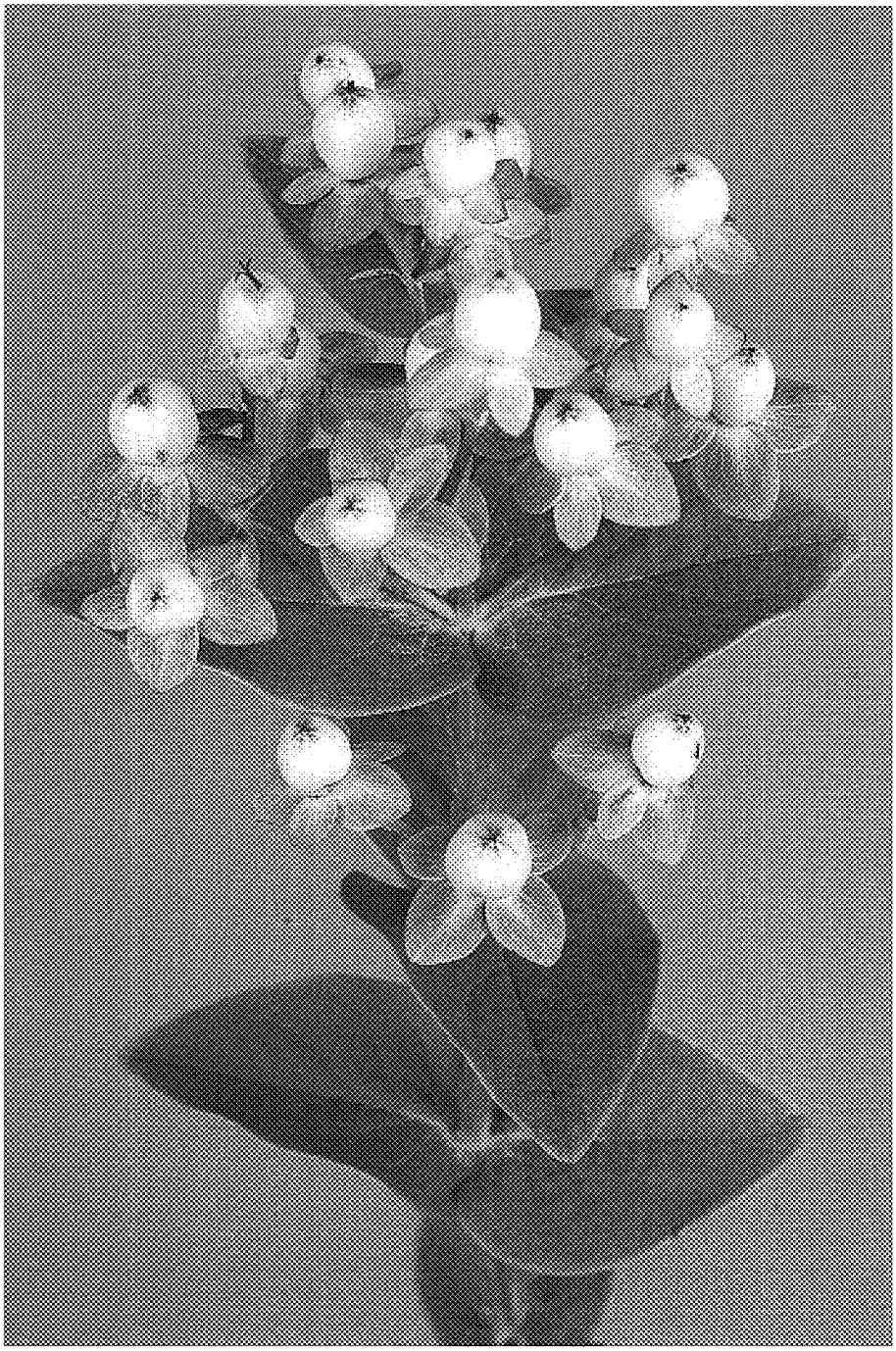

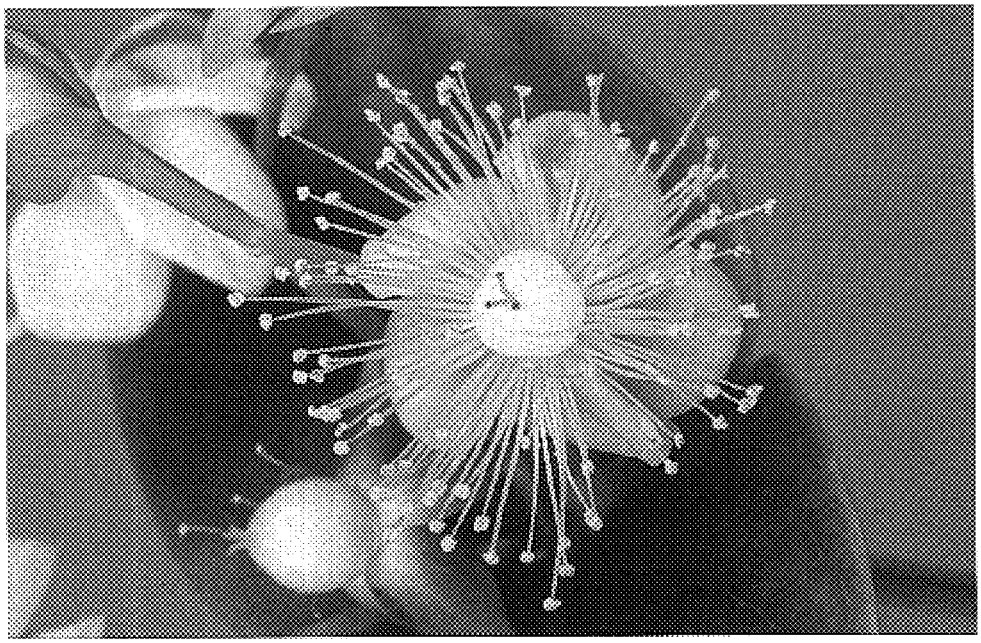
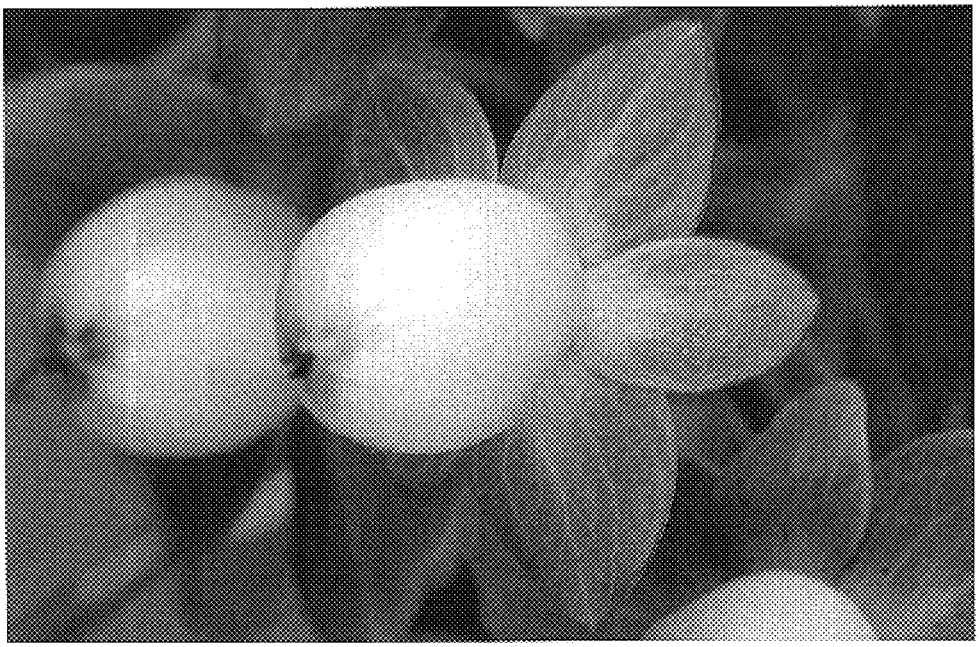

* * * * *